United States Patent [19]

Glover

[11] Patent Number: 5,792,898

[45] Date of Patent: Aug. 11, 1998

[54] PROCESS FOR THE MANAGEMENT OF MONONUCLEAR AND POLYNUCLEAR AROMATIC COMPOUNDS PRODUCED IN A HYDROCARBON DEHYDROGENATION REACTION ZONE

[75] Inventor: Bryan K. Glover, Algonquin, Ill.

[73] Assignee: UOP LLC, Des Plaines, Ill.

[21] Appl. No.: 723,204

[22] Filed: Sep. 27, 1996

[51] Int. Cl.[6] ................................. C07C 7/12; C07C 7/00
[52] U.S. Cl. ........................ 585/827; 585/655; 585/804; 585/809; 585/820
[58] Field of Search ........................ 585/655, 804, 585/809, 827, 820

[56] References Cited

U.S. PATENT DOCUMENTS

| 4,430,517 | 2/1984 | Imai et al. | 585/660 |
|---|---|---|---|
| 5,276,231 | 1/1994 | Kocal et al. | 585/804 |
| 5,481,060 | 1/1996 | Scott et al. | 585/867 |

Primary Examiner—Glenn Caldarola
Assistant Examiner—In Suk Bullock
Attorney, Agent, or Firm—Thomas K. McBride; John G. Tolomei; John G. Cutts, Jr.

[57] ABSTRACT

A process for the management of polynuclear aromatic compounds produced in a hydrocarbon dehydrogenation zone wherein the effluent from the hydrocarbon dehydrogenation zone containing dehydrogenated hydrocarbons, dehydrogenatable hydrocarbons and trace quantities of mononuclear and polynuclear aromatic hydrocarbons is admixed with a recycle stream containing mononuclear aromatic compounds and the resulting admixture is contacted with an adsorbent to reduce the concentration of mononuclear and polynuclear aromatic compounds and to produce a stream comprising dehydrogenated hydrocarbons and dehydrogenatable hydrocarbons. An off-line spent adsorbent containing mononuclear and polynuclear aromatic compounds is contacted with a hot hydrogen-rich gas to recover at least a portion of said mononuclear and polynuclear aromatic compounds to thereby regenerate the spent adsorbent.

6 Claims, 1 Drawing Sheet

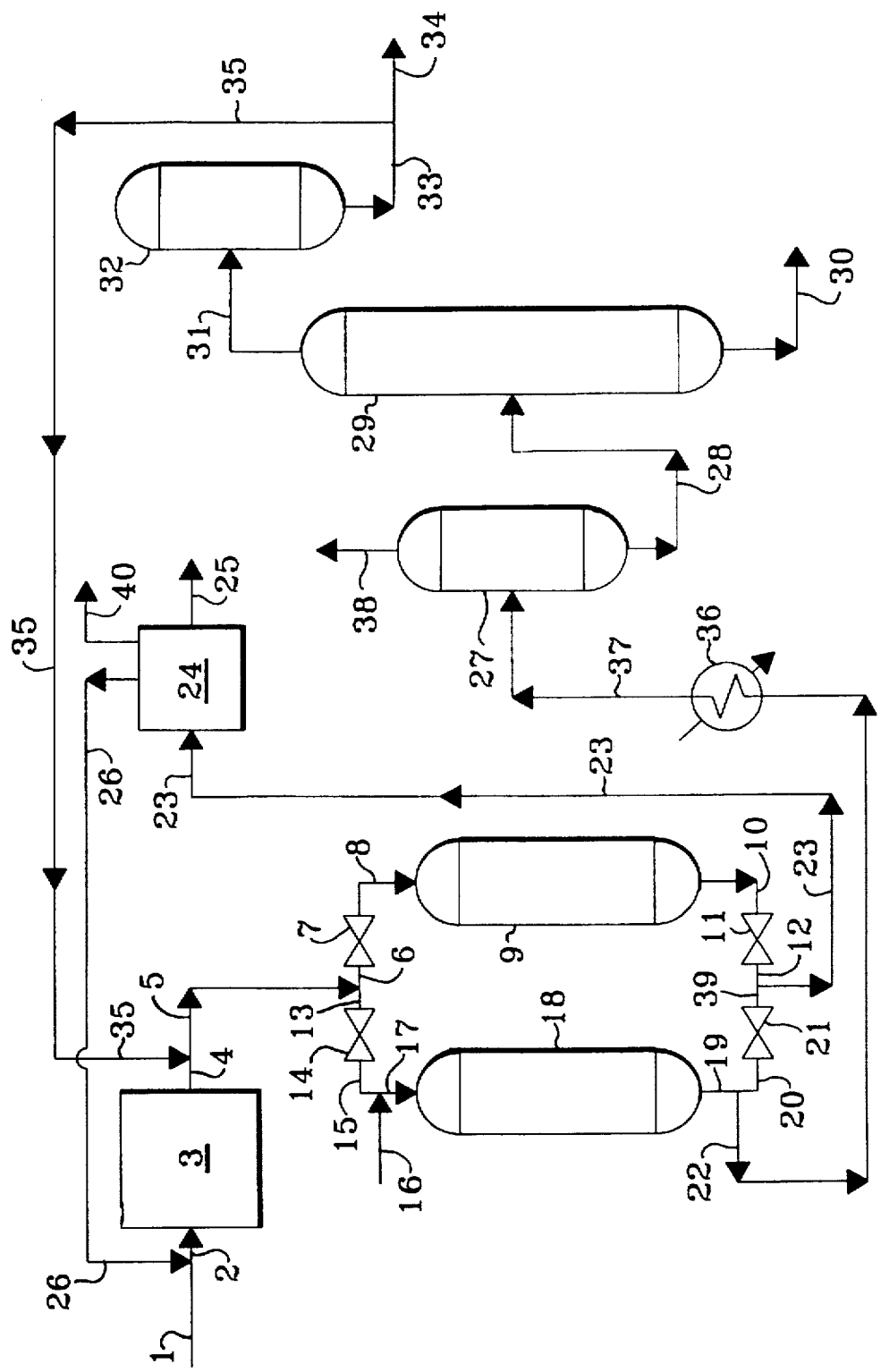

PROCESS FOR THE MANAGEMENT OF MONONUCLEAR AND POLYNUCLEAR AROMATIC COMPOUNDS PRODUCED IN A HYDROCARBON DEHYDROGENATION REACTION ZONE

FIELD OF THE INVENTION

The field of art to which this invention pertains is the removal and recovery of polynuclear aromatic compound co-products from the vapor effluent from a normally gaseous hydrocarbon dehydrogenation reaction zone.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers and other products which are well known to those skilled in the art. One example of this process is the dehydrogenation of isobutane to produce isobutylene which can be polymerized to provide tackifying agents for adhesives, viscosity-index additives for motor oils and impact-resistant and anti-oxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 issued to Imai et al discusses a dehydrogenation process and catalyst for use therein.

Despite the fact that the dehydrogenation of paraffinic hydrocarbons is well known, the more widespread usage of this processing technology and greater severity operation of existing commercial facilities has highlighted the problem which occurs in the product recovery section of hydrocarbon dehydrogenation processes. This problem is the result of the production of trace quantities of mononuclear and polynuclear aromatic compounds. The polynuclear aromatic compounds are not only an undesired impurity, but also present a severe operational problem because when they condense and plate out on the cooler surfaces of the plant, there are detrimental results. The deposits of polynuclear aromatic compounds are difficult to remove, they reduce the efficiency of heat exchangers and they may eventually lead to plugging.

In the case where the dehydrogenated compounds are used in subsequent processes, a sudden surge of the polynuclear aromatic compounds into the dehydrogenation effluent can contaminate the resulting products from the subsequent processes. The presence of polynuclear aromatic compounds changes the color quality of products and the value or marketability of the products is significantly reduced.

Therefore, those skilled in the art of hydrocarbon processing have sought methods to overcome the problem posed by the production of mononuclear and polynuclear aromatic compounds in dehydrogenation production facilities. The process of the present invention provides a facile and economical solution to the problem of the production of mononuclear and polynuclear aromatic compounds in a dehydrogenation plant.

BRIEF SUMMARY OF THE INVENTION

The present invention relates to a process for the management of polynuclear aromatic compounds produced in a hydrocarbon dehydrogenation zone wherein the effluent from the hydrocarbon dehydrogenation zone comprising dehydrogenated hydrocarbons, dehydrogenatable hydrocarbons, trace quantities of mononuclear and polynuclear aromatic hydrocarbons is admixed with a recycle stream containing mononuclear aromatic compounds and the resulting admixture is contacted with an adsorbent to reduce the concentration of mononuclear and polynuclear aromatic compounds and to produce a stream comprising dehydrogenated hydrocarbons and dehydrogenatable hydrocarbons. An off-line spent adsorbent containing mononuclear and polynuclear aromatic compounds is contacted with a hot hydrogen-rich gas to recover at least a portion of the mononuclear and polynuclear aromatic compounds to thereby regenerate the spent adsorbent. The resulting hydrogen-rich gas containing mononuclear and polynuclear aromatic compounds is separated to produce a stream containing mononuclear aromatic compounds and a stream containing polynuclear aromatic compounds. At least a portion of the stream containing mononuclear aromatic compounds is recycled as described hereinabove.

One embodiment of the present invention may be characterized as a process for the management of mononuclear and polynuclear aromatic compounds produced in a hydrocarbon dehydrogenation reaction zone which process comprises: (a) admixing the effluent from a hydrocarbon dehydrogenation reaction zone comprising dehydrogenated hydrocarbons, dehydrogenatable hydrocarbons and trace quantities of mononuclear and polynuclear aromatic hydrocarbons with a recycle stream comprising mononuclear aromatic compounds; (b) contacting the resulting admixture from step (a) with a first adsorbent and adsorbing mononuclear and polynuclear aromatic compounds to reduce the concentration of mononuclear and polynuclear aromatic compounds in the admixture and produce a stream comprising dehydrogenated hydrocarbons and dehydrogenatable hydrocarbons; (c) contacting a second adsorbent retaining adsorbed mononuclear and polynuclear aromatic compounds with a hot hydrogen-rich gas to desorb at least a portion of the mononuclear and polynuclear aromatic compounds and thereby regenerate the second adsorbent; (d) separating a stream comprising mononuclear and polynuclear aromatic compounds recovered from step (c) to produce a stream comprising mononuclear aromatic compounds and a stream comprising polynuclear aromatic compounds; and (e) recycling at least a portion of the stream comprising mononuclear aromatic compounds to provide the recycle stream in step (a).

Other embodiments of the present invention encompass further details such as preferred dehydrogenated hydrocarbons, adsorbents and operating conditions.

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the removal and recovery of trace quantities of polynuclear aromatic compounds from the vapor effluent of a hydrocarbon dehydrogenation zone. The dehydrogenation of paraffinic hydrocarbons is well known to those skilled in the art of hydrocarbon processing. In accordance with the present invention, the preferred dehydrogenated hydrocarbons are selected from the group consisting of ethylene, propylene and butylene.

In the dehydrogenation process, fresh hydrocarbon feed is combined with recycle hydrogen and recycled unconverted hydrocarbons. This forms a reactant stream which is passed through a bed of suitable dehydrogenation catalyst maintained at the proper dehydrogenation conditions such as temperature, pressure and space velocity, and the effluent from the catalytic reaction zone is processed further to yield a stream containing olefinic hydrocarbons. In accordance with the present invention, the effluent from the catalytic dehydrogenation reaction zone contains unconverted saturated hydrocarbons, olefin hydrocarbons, mononucleararomatic compounds in an amount from about 100 to about 5000 wppm and polynuclear aromatic compounds in an amount from about 50 to about 500 wppm.

In accordance with the present invention, the dehydrogenation reaction zone effluent is admixed with a recycle stream containing mononuclear aromatic compounds. The amount of the recycle stream of mononuclear aromatic compounds is selected to prevent the deposition and accumulation of polynuclear aromatic compounds on the internal surfaces of the plant downstream of the dehydrogenation reaction zone and preferably in an amount from about 0.01 to about 1 weight percent of the reaction zone effluent. The resulting admixture of the dehydrogenation reaction zone effluent and the recycle stream of mononuclear aromatic compounds is contacted with an adsorbent to reduce the concentration of mononuclear and polynuclear aromatic compounds to produce a resulting stream containing hydrogen, dehydrogenated hydrocarbons and dehydrogenatable hydrocarbons which is subsequently compressed and cooled to a temperature in the range of about −50° F. to about −200° F. to produce a hydrogen-rich gaseous stream which is preferably recycled in part to the dehydrogenation reaction zone and a stream containing dehydrogenated hydrocarbons and dehydrogenatable hydrocarbons. Any suitable adsorbent may be used in accordance with the present invention, however, preferred adsorbents are selected from the group consisting of activated alumina and activated carbon.

A spent adsorbent containing mononuclear and polynuclear aromatic compounds is contacted with a hot hydrogen-rich gas having a temperature in the range from about 300° F. (149° C.) to about 700° F. (371° C.) to desorb at least a portion of the aromatic compounds contained thereon. The resulting stream of hydrogen and mononuclear and polynuclear aromatic compounds is cooled to a temperature in the range of −60° F. (16° C.) to about 120° F. (49° C.) and introduced in a vapor-liquid separation zone to produce a hydrogen-rich gaseous stream which may be recycled if desired. The hydrogen-rich gas is preferably a portion of the net hydrogen off-gas generated in the dehydrogenation reaction zone. A liquid stream containing mononuclear and polynuclear aromatic compounds is removed from the vapor-liquid separation zone and separated, preferably by fractionation, to produce a stream of polynuclear aromatic compounds and a stream containing mononuclear aromatic compounds, at least a portion of which is used as the hereinabove-described recycle stream. Since mononuclear aromatic compounds are produced as a by-product in the dehydrogenation reaction zone, a net stream comprising mononuclear aromatic compounds is produced and removed from the process.

DETAILED DESCRIPTION OF THE DRAWING

With reference now to the drawing, a normally gaseous dehydrogenatable hydrocarbon feedstock is introduced into the process via conduit 1 and is admixed with a recycle hydrogen stream provided via conduit 26 and the resulting admixture is introduced via conduit 2 into dehydrogenation zone 3. A resulting effluent from dehydrogenation zone 3 containing dehydrogenated hydrocarbons, dehydrogenatable hydrocarbons and trace quantities of mononuclear and polynuclear aromatic hydrocarbons is transported via conduit 4 and admixed with a recycle stream containing mononuclear aromatic compounds provided via conduit 35 and the resulting admixture is transported via conduit 5, conduit 6, valve 7 and conduit 8 and introduced into adsorbent zone 9. A resulting hydrocarbon stream containing a reduced concentration of mononuclear and polynuclear aromatic compounds is removed from adsorption zone 9 and transported via conduit 10, valve 11, conduit 12 and conduit 23 and is introduced into vapor-liquid separation zone 24. A hydrogen-rich gaseous stream is removed from vapor-liquid separation zone 24 via conduit 26 and recycled as described hereinabove. A net hydrogen gas stream is removed from vapor-liquid separation zone 24 via conduit 40. A liquid hydrocarbon stream containing dehydrogenated hydrocarbons and dehydrogenatable hydrocarbons is removed from vapor-liquid separation zone 24 via conduit 25 and recovered. A hot hydrogen-rich gaseous stream is introduced via conduits 16 and 17 into off-line adsorption zone 18. A resulting hydrogen gaseous stream containing desorbed mononuclear and polynuclear aromatic compounds is removed from adsorption zone 18 via conduit 19, conduit 22 and introduced into heat exchanger 36. The resulting cooled effluent from heat exchanger 36 is transported via conduit 37 and introduced into vapor-liquid separation zone 27. A hydrogen-rich gaseous stream is removed from vapor-liquid separation zone 27 via conduit 38. A liquid stream containing mononuclear and polynuclear aromatic compounds is removed from vapor-liquid separation zone 27 via conduit 28 and introduced into fractionation zone 29. A stream containing polynuclear aromatic compounds is removed from fractionation zone 29 via conduit 30 and recovered. A stream containing mononuclear aromatic compounds is removed from fractionation zone 29 via conduit 31 and introduced into receiver 32. A stream containing mononuclear aromatic compounds is removed from receiver 32 via conduits 33 and 35 and recycled as hereinabove described. A net stream containing mononuclear aromatic compounds is removed from receiver 32 via conduits 33 and 34 and recovered. Conduits 13 and 6, in conjunction with valve 14, and conduits 20 and 39, in conjunction with valve 21, are utilized when adsorption zone 18 is put on line to replace adsorption zone 9 during its regeneration.

ILLUSTRATIVE EMBODIMENT

An isobutane feed stream in an amount of 100 mass units per hour is introduced into a dehydrogenation zone to convert 50 weight percent of the feed to isobutylene. Recycle hydrogen is also introduced into the dehydrogenation zone in an amount of 900 SCFB. The resulting effluent from the dehydrogenation zone contains 1000 ppm mononuclear aromatic compounds and 200 ppm of polynuclear aromatic compounds based on hydrocarbon and is admixed with a recycle stream containing mononuclear aromatic compounds in an amount of 0.05 mass units per hour. The resulting admixture of effluent from the dehydrogenation zone and the recycle stream is introduced into an adsorption zone containing activated alumina to reduce the level of mononuclear aromatic compounds to less than 500 ppm and the level of polynuclear aromatic compounds to less than 1 ppm. The resulting effluent from the adsorption zone is compressed and cooled to a temperature of −130° F. which is subsequently introduced into a vapor-liquid separation zone to produce a hydrogen-rich gaseous stream which is recycled to the dehydrogenation zone and a liquid hydrocarbon stream containing isobutane and isobutylene.

A hot hydrogen-rich gaseous stream having a temperature of 600° F. (315° C.) is introduced into a spent, off-line adsorption zone containing an activated alumina with adsorbed mononuclear and polynuclear aromatic compounds in order to regenerate the adsorption zone. The resulting hydrogen stream containing mononuclear and polynuclear aromatic compounds is cooled to 100° F. (38° C.) to condense the aromatic compounds and introduced into a vapor-liquid separation zone to produce a hydrogen stream and a liquid stream containing mononuclear and polynuclear aromatic compounds which liquid stream is fractionated to produce a stream containing polynuclear aromatic compounds and a stream containing mononuclear aromatic compounds. A portion of the stream containing mononuclear aromatic compounds is recycled as described hereinabove. A net stream containing mononuclear aromatic compounds is recovered and removed from the process.

The foregoing description and illustrative embodiment clearly illustrate the advantages encompassed by the method of the present invention and the benefits to be afforded with the use thereof.

What is claimed:

1. A process for the management of mononuclear and polynuclear aromatic compounds produced in a hydrocarbon dehydrogenation reaction zone which process comprises:

(a) admixing the effluent from a hydrocarbon dehydrogenation reaction zone comprising dehydrogenated hydrocarbons, dehydrogenatable hydrocarbons and trace quantities of mononuclear and polynuclear aromatic hydrocarbons with a recycle stream comprising mononuclear aromatic compounds;

(b) contacting the resulting admixture from step (a) with an adsorbent and adsorbing mononuclear and polynuclear aromatic compounds to reduce the concentration of mononuclear and polynuclear aromatic compounds in said admixture and produce a stream comprising dehydrogenated hydrocarbons and dehydrogenatable hydrocarbons;

(c) contacting said adsorbent retaining adsorbed mononuclear and polynuclear aromatic compounds with a hot hydrogen-rich gas to desorb at least a portion of said mononuclear and polynuclear aromatic compounds and thereby regenerate said second adsorbent;

(d) separating a stream comprising mononuclear and polynuclear aromatic compounds recovered from step (c) to produce a stream comprising mononuclear aromatic compounds and a stream comprising polynuclear aromatic compounds; and (e) recycling at least a portion of said stream comprising mononuclear aromatic compounds to provide said recycle stream in step (a).

2. The process of claim 1 wherein said dehydrogenated hydrocarbons are selected from the group consisting of ethylene, propylene and butylene.

3. The process of claim 1 wherein said polynuclear aromatic compounds are present in the effluent from a hydrocarbon dehydrogenation reaction zone in an amount from about 50 to about 500 wppm.

4. The process of claim 1 wherein step (b) is conducted at a temperature from about 50° F.(10° C.) to about 150° F.(65° C.).

5. The process of claim 1 wherein said adsorbent is selected from the group consisting of activated alumina and activated carbon.

6. The process of claim 1 wherein said recycle stream comprising mononuclear aromatic compounds is present in an amount from about 0.01 to about 1 weight percent of said effluent from a hydrocarbon dehydrogenation reaction zone.

* * * * *